United States Patent [19]

Zanotti

[11] Patent Number: 5,084,034

[45] Date of Patent: Jan. 28, 1992

[54] METHOD FOR SAMPLING BODY FLUIDS

[75] Inventor: Leah M. Zanotti, Wakefield, Mass.

[73] Assignee: Tufts University, Medford, Mass.

[21] Appl. No.: 535,081

[22] Filed: Jun. 8, 1990

[51] Int. Cl.$^5$ .................. A61M 1/00; A61M 31/00; A61B 5/00

[52] U.S. Cl. .................. 604/319; 128/762; 604/53

[58] Field of Search .................. 604/317–321, 604/53; 128/762–764

[56] References Cited

U.S. PATENT DOCUMENTS

| | | | |
|---|---|---|---|
| 3,136,314 | 8/1960 | Kravitz | 128/253 |
| 3,674,011 | 7/1972 | Michel et al. | 128/2 F |
| 3,774,604 | 11/1973 | Danielsson | 604/53 X |
| 3,848,581 | 11/1974 | Cinqualbre et al. | 128/2 F |
| 3,866,608 | 2/1975 | Reynolds et al. | 604/319 X |
| 3,890,101 | 6/1975 | Tiffany et al. | 23/259 |
| 3,891,416 | 6/1975 | Leonard et al. | 604/317 X |
| 4,207,870 | 6/1980 | Eldridge | 128/766 |
| 4,257,416 | 3/1981 | Prager | 128/214 R |
| 4,263,922 | 4/1981 | White | 128/763 |
| 4,306,705 | 12/1981 | Svensson | 604/317 X |
| 4,393,882 | 7/1983 | White | 128/764 |
| 4,421,123 | 12/1983 | Percarpio | 128/766 |
| 4,643,192 | 2/1987 | Fiddian-Green | 128/632 |
| 4,650,457 | 3/1987 | Morioka et al. | 604/4 |
| 4,696,309 | 9/1987 | Stephan | 128/762 |
| 4,718,423 | 1/1988 | Willis et al. | 128/634 |
| 4,803,999 | 2/1989 | Liegner | 128/763 |
| 4,850,961 | 7/1989 | Wanderer et al. | 604/53 |
| 4,871,355 | 10/1989 | Kikkawa | 604/198 |

FOREIGN PATENT DOCUMENTS

| | | | |
|---|---|---|---|
| 1093933 | 1/1981 | Canada | 604/53 |
| 1202197 | 3/1986 | Canada | 604/53 |
| 0336853 | 10/1989 | European Pat. Off. | 604/53 |

Primary Examiner—David J. Isabella
Assistant Examiner—Elizabeth M. Burke
Attorney, Agent, or Firm—Fish & Richardson

[57] ABSTRACT

In general, the invention is an improved device and method of obtaining body fluid samples from an indwelling catheter. A valve having ports for attachment of a catheter, attachment of a fluid line, and collection of fluids has positions that allow fluid to be removed from the catheter, fluid to be removed from the fluid line, and fluid in the fluid line to be introduced into the catheter. A connector inserted in the collection port forms a fluid-tight seal with the collection port and communicates with a needle which protrudes outwardly in a manner that allows the needle to penetrate a sealing member. Protective means associated with the needle prevents inadvertent contact by the user with the needle or with fluid adhered to the needle. The needle is constructed to removably receive a vacuum collection tube with a penetrable sealing member in a manner that penetrates the sealing member and applies the force of the vacuum of the tube to the needle and to the collection port.

4 Claims, 3 Drawing Sheets

FIG. I

DISCARD TUBE (FOR CLEARING LINE)

SAMPLE TUBE (FOR BODY FLUID)

DISCARD TUBE
(FOR CLEARING LINE)

SAMPLE TUBE
(FOR BODY FLUID)

DISCARD TUBE
(FOR FLUSHING LINE)

METHOD FOR SAMPLING BODY FLUIDS

BACKGROUND OF THE INVENTION

This invention relates to obtaining blood or other body fluid samples from an indwelling catheter.

The growing concern of hepatitis and HIV exposure has made the medical community more aware of the risks of exposure to blood and blood products. It is the responsibility of the medical community to obtain, handle, and dispose of blood samples and blood collection devices in accordance with the universal precautions recommendations of the Center for Disease Control (CDC) and other procedures to minimize the risk of exposure to blood products.

Typically, to obtain blood samples from indwelling intravenous and arterial catheters, successive syringes are attached to a stopcock or valve attached to the indwelling catheter to clear the patient line of saline, medication, or old blood and to obtain the desired number of blood samples.

SUMMARY OF THE INVENTION

In general, the invention is an improved device and method of obtaining body fluid samples from an indwelling catheter. A valve having ports for attachment of a catheter, attachment of a fluid line, and collection of fluids has positions that allow fluid to be removed from the catheter, fluid to be removed from the fluid line, and fluid in the fluid line to be introduced into the catheter. A connector inserted in the collection port forms a fluid-tight seal with the collection port and communicates with a needle which protrudes outwardly in a manner that allows the needle to penetrate a sealing member. Protective means associated with the needle prevents inadvertent contact by the user with the needle or with fluid adhered to the needle. The needle is constructed to removably receive a vacuum collection tube with a penetrable sealing member in a manner that penetrates the sealing member and applies the force of the vacuum of the tube to the needle and to the collection port.

DESCRIPTION OF THE PREFERRED EMBODIMENT

Figure 1:
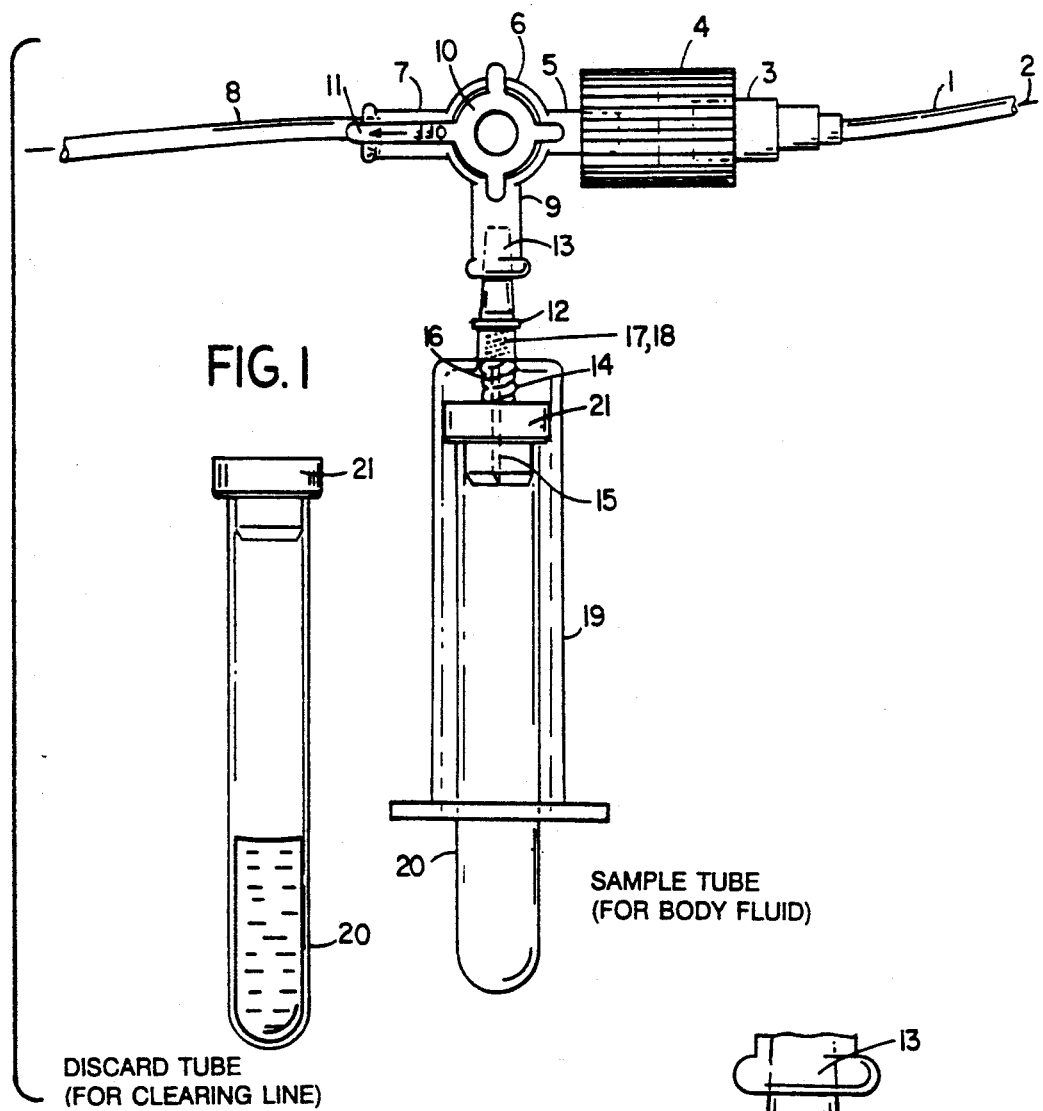
FIG. 1 is an elevational view of an embodiment of the invention positioned to withdraw fluid from a catheter.
Figure 2:
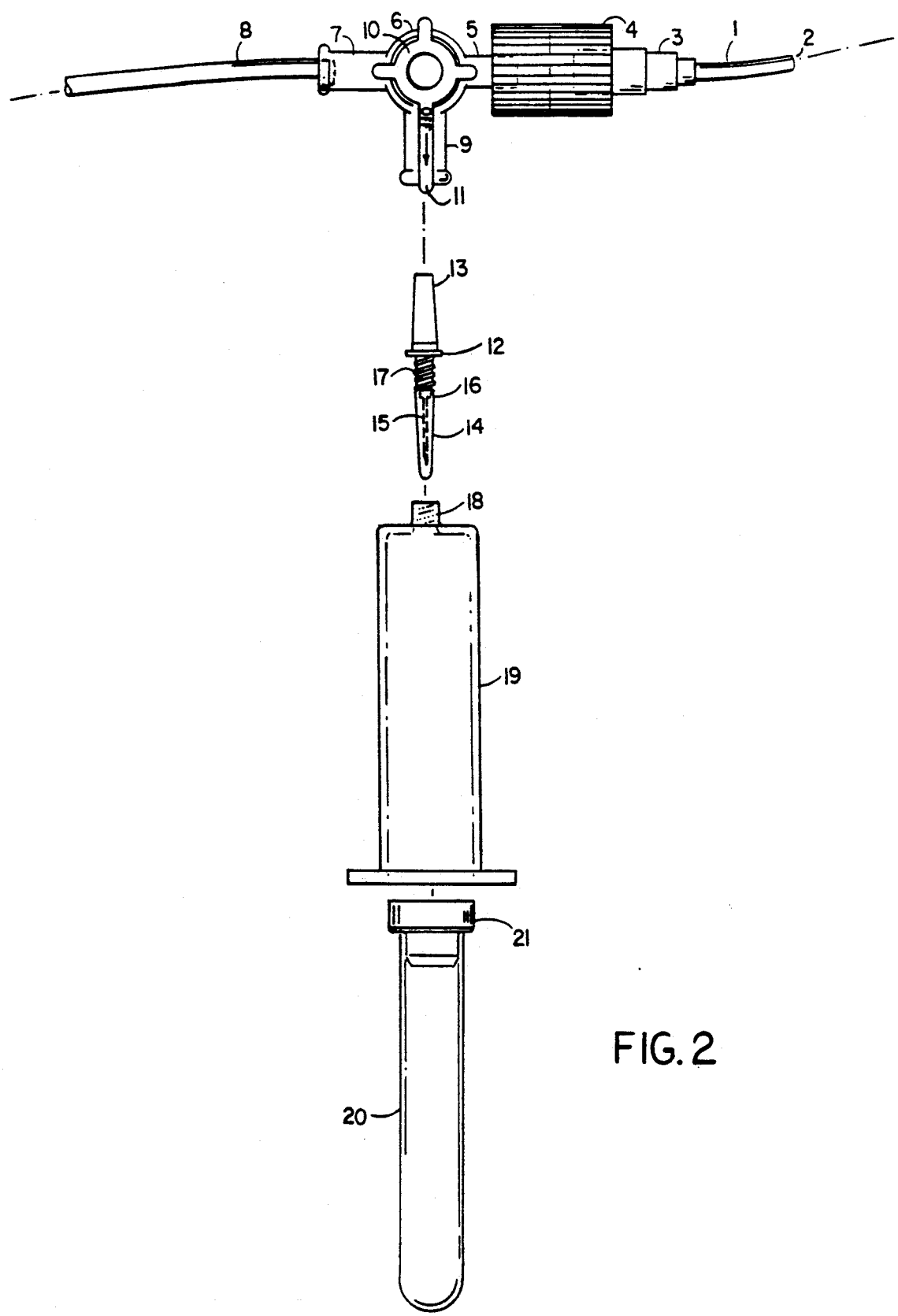
FIG. 2 is an elevational view of an embodiment of the invention prior to assembly and positioned to administer fluid to the patient.
Figure 3:
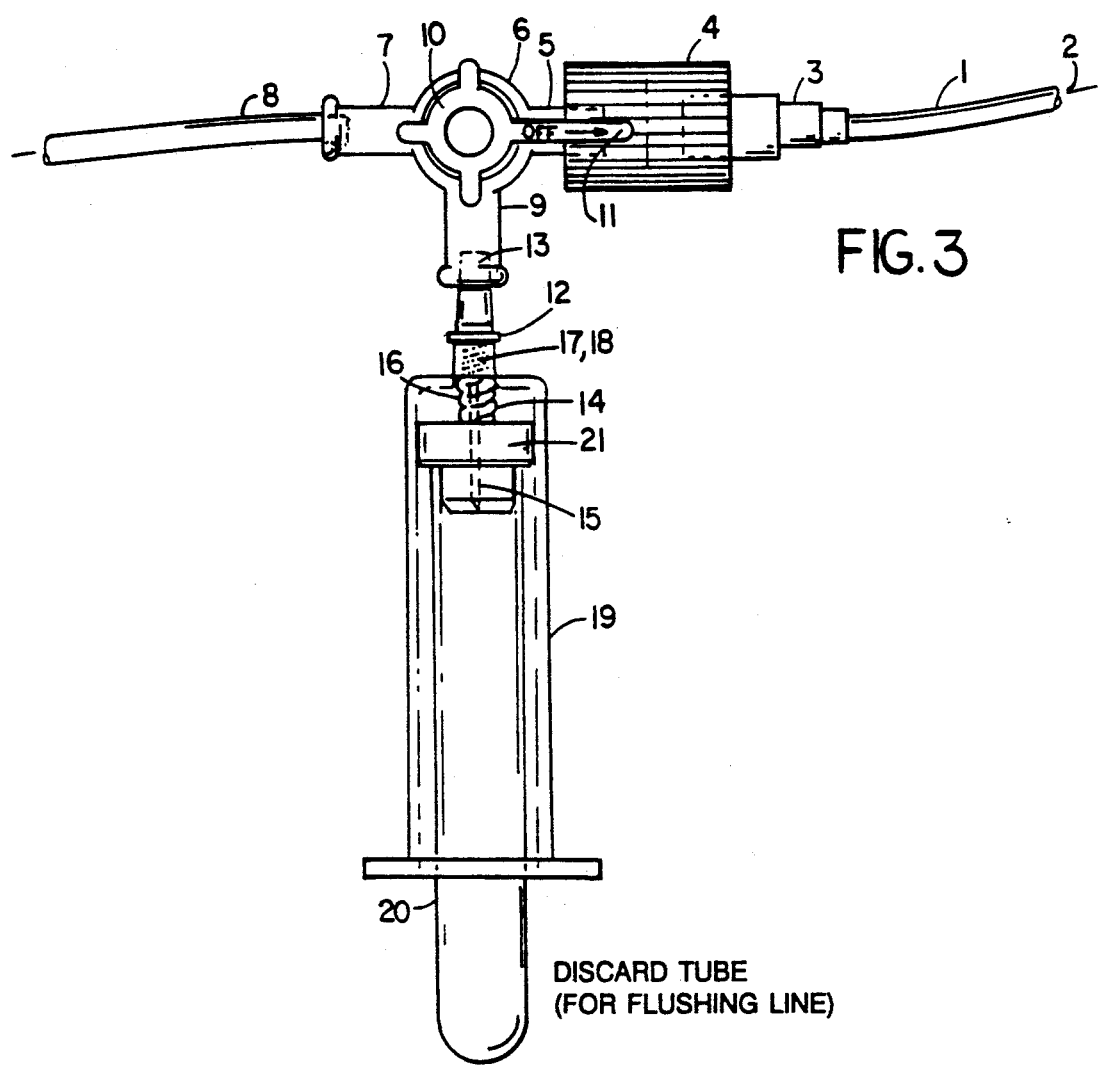
FIG. 3 is an elevational view of an embodiment of the invention positioned to withdraw fluid from a fluid line.

Indwelling venous or arterial catheters may be placed in a patient, for example, where periodic blood samples are required or to monitor blood pressure. Referring to FIG. 1, an indwelling catheter 1 is inserted in the patient's vein or artery at one end 2 and is attached at its other end 3 by a connector 4 to a port 5 of a four-way stopcock 6 such as a Burron Discofix® 4-way stopcock. The stopcock 6 has a second port 7 that is attached to a fluid line 8. The stopcock has a third port 9 that can be used as a collection port or to attach an additional fluid line. The stopcock has a valve 10 that can be positioned as shown in FIGS. 1, 2, and 3. Referring to FIG. 2, an indicator 11 points in the direction of collection port 9, indicating that flow to collection port 9 is closed and that flow is open between fluid line 8 and the indwelling catheter 1. In this position, fluid line 8 may be used to administer medication to the patient. Alternately, a saline solution may be administered through the fluid line 8 to keep the indwelling catheter 1 open and prevent blood from clotting. The valve 10 may also be positioned as in FIG. 1 to allow flow between the indwelling catheter 1 and collection port 9 or, as shown in FIG. 3, to allow flow between the fluid line 8 and collection port 9.

An adaptor 12, such as the Vacutainer Brand Luer Adaptor made for blood draw directly from a needle inserted in a patient's vein, with a tapered, hollow end 13 is inserted in collection port 9. The adaptor 12 is sized so that the tapered, hollow end 13 creates an interference fit with the sample port 9 sufficient to prevent leakage of fluid between the collection port 9 and the adaptor end 13. The adaptor 12 has a needle end 14 which consists of a hollow needle 15 which communicates with the hollow, tapered end 13 and which is encased in a protective, retractable rubber sheath 16 which protects the user from contact with the needle 15 and prevents leakage of blood from the needle 15. The adaptor 12 has threads 17 which cooperate with the threads 18 of a protective polypropylene sleeve 19, such as the Terumo Venoject® Polypropylene Holder, allowing attachment of the sleeve 19 to the adaptor 12 and further protecting the user from contact with the needle 15 and any blood adhering to the needle 15.

Figure 4:
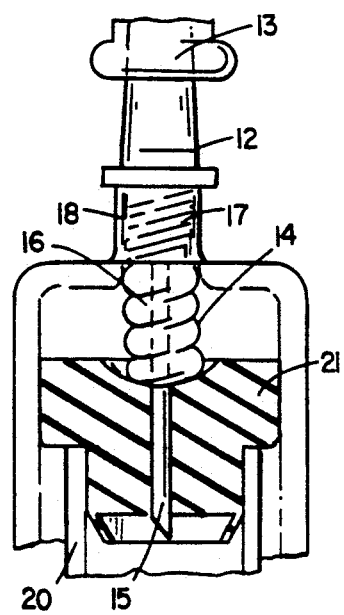
FIG. 4 is a cross-sectional detail of the invention shown in FIGS. 1 and 3.

A sealed evacuated tube 20 such as the 5 milliliter Vacutainer Brand Silicon-coated tube with a rubber cap 21 is inserted in sleeve 19. Referring to FIG. 4, when the tube 20 is inserted, the cap 21 pushes down rubber sheath 16, allowing the needle 15 to penetrate the cap 21 and puncture the seal of tube 20.

Referring to FIG. 2, which shows the device prior to assembly, the device is assembled by attaching adaptor 12 to the sleeve 19 and inserting adaptor 12 into the collection port 9 of the stopcock 6.

Referring to FIG. 1, to clear the indwelling catheter 1 of saline, medication, or old blood, tube 20 is inserted into the sleeve 19. As the tube 20 is inserted in the sleeve 19, the rubber sheath 16 is pushed down by the cap 21 and the needle 15 punctures the seal of the tube 20. Valve 10 of stopcock 6 is turned from the position shown in FIG. 2 to the position shown in FIG. 1. The force of the vacuum draws fluid evenly from the indwelling catheter 1 into the tube 20. To clear the catheter 1 of saline, medication, or old blood, the user will need to withdraw approximately 1½-2 milliliters of fluid. When fresh blood begins to enter tube 20, tube 20 is removed with a twisting motion. As tube 20 is removed, the rubber sheath 16 extends and covers needle 15, preventing leakage of or exposure to blood. This partially filled tube 20, referred to as a discard tube, is retained for use in flushing the system after all samples are collected.

Referring again to FIG. 1, to obtain blood samples, required size sample tube 20 is inserted into sleeve 19, again puncturing the cap 21 of the tube with the needle 15. After tube 20 is filled, remove the tube 20, referred to as a sample tube, with a twisting motion. Repeat this step for as many sample tubes as needed.

When the desired number of samples have been obtained and all the sample tubes have been removed from the sleeve 19, valve 10 is positioned as shown in FIG. 2 to stop the flow of blood from the indwelling catheter 1 and to allow fluid in fluid line 8 to flow to the indwelling catheter 1.

Using the retained discard tube which was used to clear the indwelling catheter 1 of saline, medication, or old blood, the discard tube 20 is inserted into the sleeve 19. Valve 10 is positioned as shown in FIG. 3. The remaining vacuum in discard tube 20 draws fluid in fluid line 8 through the stopcock 6, the collection port 9, and adaptor 12 flushing and cleaning the device of blood particles that may have adhered during sampling.

When the discard tube is filled, valve 10 is again positioned as shown in FIG. 2, allowing fluid in the fluid line 8 to flow to the indwelling catheter 1. Alternately, the flushing step may be repeated with additional evacuated tubes. The discard tube or tubes are removed and placed in a container for biohazard waste disposal.

The sleeve 19 and adaptor 12 assembly are removed from the stopcock 6 and are discarded in accordance with procedures for blood-contaminated products.

The device and method are advantageous because multiple blood samples may be obtained in a virtually closed system. The device and method expedite obtaining blood samples because the valve may remain in one position while all samples are obtained as compared to, for example, use of multiple syringes which require the user to shut off the flow of blood before each syringe is detached and turn on the flow of blood after the successive syringe is attached. The device facilitates flushing and cleaning the system of adhering blood particles which create a risk of exposure to disease. The use of evacuated tubes to withdraw blood is particularly advantageous in its application to multiple blood samples because the vacuum exerts even pressure on the vein or artery, reducing the risk of collapse or damage to the vein or artery from excessive or uneven pressure. The disposable polypropylene sleeve, adaptor, and tube are also relatively inexpensive, reducing the cost of obtaining multiple blood samples, for example, as compared to use of syringes for multiple blood samples.

This invention can be adapted to pediatric and animal use by appropriate sizing of the intravenous catheter, stopcock and adaptor. This invention is also applicable to sampling any other body fluid accessed by an indwelling catheter, for example, spinal fluid and amniotic fluid, where the risk of exposure to the fluid must be minimized or where the other advantages of the present invention are desirable.

What is claimed is:

1. A method for obtaining at least one sample of body fluid from an indwelling catheter comprising
attaching to said indwelling catheter a valve having a port for attachment to an indwelling catheter, a port for attachment of a second fluid line, and a port for collection of fluids, said valve having at least a first position that allows body fluid to be removed from said indwelling catheter, a second position that allows a second fluid to be introduced into said indwelling catheter, and a third position that allows said second fluid to flow through said collection port,
attaching a source of sterile fluid to said second fluid port,
attaching to said valve a connector inserted in the collection port of said valve comprising an inserted fluid passage defining portion that forms a fluid-tight seal with the wall defining said port,
a penetrating needle in communication with said fluid passage of said connector and protruding outwardly in a manner permitting it to pierce a sealing member, said needle associated with protective means preventing inadvertent contact by the user with the needle or with fluid adhered thereto,
and said needle constructed to removably receive a vacuum collection tube with a penetrable sealing member in a manner permitting said needle to penetrate said sealing member and to apply the vacuum of said tube, to the needle, and therefrom to said collection port,
removably attaching said tube in a manner permitting said needle to penetrate said sealing member,
positioning said valve in said first position,
applying the vacuum of said tube to draw fluid from the indwelling catheter into said tube until the desired quantity of fluid is obtained,
positioning said valve in said second position,
removing said tube from said needle,
removably attaching a second vacuum collection tube with a penetrable sealing member in a manner permitting said needle to penetrate said sealing member,
positioning said valve in said third position,
applying the vacuum of said second tube to draw said sterile second fluid into said second tube until the desired quantity of said sterile second fluid is obtained,
positioning said valve in said second position,
and removing said second tube from said needle.

2. The method of claim 1 wherein the body fluid is blood.

3. The method of claim 1 wherein the valve is a four way stopcock.

4. The method of claim 1 wherein the connector is a luer adaptor.

* * * * *